(12) United States Patent
Kushnir et al.

(10) Patent No.: US 7,513,875 B2
(45) Date of Patent: Apr. 7, 2009

(54) METHOD AND SYSTEM FOR MANAGING MECHANICAL RESPIRATORY VENTILATION

(75) Inventors: Igal Kushnir, Pardes Hana (IL); Meir Botbol, Pardes Hana (IL)

(73) Assignee: Deepbreeze Ltd., Or Akiva (IL)

( * ) Notice: Subject to any disclaimer, the term of this patent is extended or adjusted under 35 U.S.C. 154(b) by 498 days.

(21) Appl. No.: 11/253,786

(22) Filed: Oct. 20, 2005

(65) Prior Publication Data
US 2006/0086358 A1  Apr. 27, 2006

Related U.S. Application Data

(60) Provisional application No. 60/619,925, filed on Oct. 20, 2004.

(51) Int. Cl.
*A61B 5/08* (2006.01)
(52) U.S. Cl. .................... 600/538; 600/529; 600/539; 128/204.23
(58) Field of Classification Search ............ 128/204.23; 600/529–543
See application file for complete search history.

(56) References Cited

U.S. PATENT DOCUMENTS

| | | | | |
|---|---|---|---|---|
| 4,323,064 A | * | 4/1982 | Hoenig et al. | 128/204.21 |
| 4,972,842 A | * | 11/1990 | Korten et al. | 600/529 |
| 5,259,373 A | * | 11/1993 | Gruenke et al. | 128/204.23 |
| 5,562,101 A | * | 10/1996 | Hankinson et al. | 600/538 |
| 5,797,393 A | * | 8/1998 | Kohl | 128/204.23 |
| 5,941,841 A | * | 8/1999 | Mutch et al. | 604/4.01 |
| 6,019,732 A | * | 2/2000 | Volgyesi | 600/534 |
| 6,139,505 A | | 10/2000 | Murphy | |
| 6,241,683 B1 | * | 6/2001 | Macklem et al. | 600/529 |
| 6,431,171 B1 | * | 8/2002 | Burton | 128/204.18 |
| 2001/0035186 A1 | | 11/2001 | Hill | |
| 2003/0139679 A1 | | 7/2003 | Kushnir et al. | |
| 2005/0182337 A1 | * | 8/2005 | Botbol et al. | 600/538 |

OTHER PUBLICATIONS

Soufflet, G., et al., "Interaction Between Tracheal Sound and Flow Rate: A Comparison of Some Different Flow Evaluations from Lung Sounds", *IEEE Transactions on Biomedical Engineering*, vol. 37, No. 4, pp. 384-390, (1990).

* cited by examiner

*Primary Examiner*—Robert L Nasser
*Assistant Examiner*—Karen E Toth
(74) *Attorney, Agent, or Firm*—The Nath Law Group; Jerald L. Meyer; Derek Richmond

(57) ABSTRACT

A system and computer implemented method for operating a respiratory ventilator ventilating a subject. One or more body signals obtained from the subject indicative of the subject's ventilation are analyzed so as to perform a spirometric assessment of the ventilation. It is then determined whether the spirometric assessment satisfactorily conforms to one or more predetermined spirometric standards. If the spirometric assessment does not satisfactorily conform to the spirometric standard, the operating parameters of the ventilator are adjusted. The invention also provides a system for carrying out the method.

18 Claims, 2 Drawing Sheets

METHOD AND SYSTEM FOR MANAGING MECHANICAL RESPIRATORY VENTILATION

This application claims the benefit of prior U.S. provisional patent application No. 60/619,925 filed Oct. 20, 2004, the contents of which are hereby incorporated by reference in their entirety.

FIELD OF THE INVENTION

The present invention relates to respiratory mechanical ventilation and to methods of operating a respiratory ventilator.

BACKGROUND OF THE INVENTION

Respiratory ventilators are used to provide mechanical ventilation to a subject. The ventilation is employed to assist, or in some cases replace, spontaneous breathing. This ventilation can be life-saving and is a mainstay of intensive care medicine as well as during anesthesia.

A respiratory ventilator comprises a compressible air reservoir, air and oxygen supplies, a set of valves and tubes. The air reservoir is compressed several times a minute to deliver a mixture of air, oxygen, and/or other gases to the patient. When the overpressure is released, the patient exhales passively due to the elasticity of the lungs. The oxygen content of the inspired gas can be set from 21 percent (ambient air) to 100 percent (pure oxygen). The pressure and flow characteristics of the ventilator can be set mechanically or electronically.

In continuous mandatory ventilation, breaths are delivered at preset intervals, regardless of patient effort. This mode is utilized most often in the paralyzed or apneic patient because it can enhance breathing if respiratory efforts are present. In assist-control ventilation, the ventilator delivers preset breaths in coordination with the respiratory effort of the patient. With each inspiratory effort, the ventilator delivers a full assisted tidal volume. In this case, spontaneous breathing independent of the ventilator between breaths is not allowed.

In synchronous intermittent mandatory ventilation, the ventilator delivers preset breaths in coordination with the respiratory effort of the patient. Spontaneous breathing is allowed between breaths. The synchronization attempts to limit the barotrauma, which may occur with IMV when a preset breath is delivered to a patient who is already maximally inhaled (breath stacking) or is forcefully exhaling.

The operational parameters of the ventilator should be set so that the characteristics of the ventilation delivered to the subject (such as the pressure and flow rates) are optimized for the subject's individual needs. However, it is often not possible to assess the subject's individual requirements. Moreover, it is often not possible to know how the operational parameters of the ventilator should be set in order to achieve an optimal ventilation.

The term "spirometry" refers to a common test of respiratory function that involves measuring the total volume of air inhaled into the lungs over a respiratory cycle. A spirometry test is usually carried out by having a subject inhale air through a tube connected to an air flow meter that measures the total volume of air inhaled during the inspiration phase of the respiratory cycle. At the termination of the inspiration phase the subject exhales through the tube. A curve is generated showing the air flow as a function of time. The curve is analyzed to obtain one or more respiratory parameters of the subject that are used to assess the state of the respiratory system.

U.S. Patent entitled, "Method and system for analyzing respiratory tract air flow", filed on Feb. 4, 2004 and having the publication number 2005017791 discloses a method for carrying out spirometry in at least a portion of an individual's respiratory tract. A plurality of microphones is fixed onto a subject's back or chest over the portion of the respiratory tract, and respiratory tract sounds are recorded from the region over a time interval from $t_0$ to $t_1$. An average acoustic energy during the subinterval is determined at a plurality of locations x in the region. The term "acoustic energy" at a location is used herein to refer to a parameter indicative of or approximating the product of the pressure and the mass propagation velocity at that location. The total average acoustic energy, summed over the locations x is then correlated with the airflow in the portion of the respiratory tract. The airflow may be calculated, for example, as to the logarithm of the total acoustic energy. The process may then be repeated during the expiratory phase of the respiratory cycle. The airflow in the lungs as a function of time during the inspiratory phase obtained may be integrated from a time $t_0$ to a time t to produce a total volume of air that has flowed into the airways from time $t_0$ to t. The airflow at a time t may be plotted as a function of the total volume of air that has flowed into the airways from $t_0$ to time t, to produce a spirometry curve for inspiration. The process may then be repeated for the expiratory phase of the respiratory cycle.

SUMMARY OF THE INVENTION

The present invention provides a method and system for operating and managing a respiratory ventilator. In accordance with the invention, one or more body signals are obtained of a subject being ventilated by a ventilator indicative of the subject's ventilation. The signals are analyzed so as to obtain a spirometric assessment of the subject's ventilation. The spirometric assessment may provide, for example, an indication of a rate of airflow into or out of the subject's respiratory system. The obtained spirometric assessment is compared to a predetermined spirometric standard. If the obtained spirometric assessment is found not to conform to the predetermined spirometric standard, the operating parameters of the ventilator are adjusted so as to alter the ventilation of the subject by the ventilator so that the ventilation of the subject better conforms to the predetermined spirometric standard. The operating parameters of the ventilator may be, for example, one or more of the an air flow rate into the subject's respiratory tract, an air flow rate out of the respiratory tract, a duration of an inspiratory phase of a respiratory cycle, respiratory rate, inspiration/expiration ratio, positive end-expiratory pressure, volume of air in the respiratory tract at any particular state of the breathing cycle, and a duration of an expiratory phase of a respiratory cycle. Thus, for example, if the spirometric assessment shows that the actual inspiration/expiration ratio of the subject significantly deviates from a predetermined inspiration/expiration ratio standard, the operating parameters of the ventilator may be adjusted so as to ventilate the subject with an inspiration/expiration ratio closer to that of the standard.

The spirometric analysis of the signals may be determined by any method of spirometric analysis of respiratory tract signals. In a presently preferred embodiment of the invention, the body signals are acoustical signals upon which a spirometric analysis is performed. This may involve determining a total acoustic energy on a body surface overlying the subject's respiratory system, as disclosed in Applicant's co-pending application Ser. No. 10/771,139, entitled, "Method and system for analyzing respiratory tract air flow", filed on Feb. 4, 2004, the contents of which are incorporated herein by reference and having the Publication No. 2005017791

The spirometric standard may be, for example, a value of a flow rate of air into the respiratory tract, a maximum volume of air inspired into the lungs during a single inspiratory phase of the respiratory cycle. The spirometric standard may be obtained, for example, from a predetermined table that gives the spirometric standard according to a subject's weight, height and/or age. The spirometric standard may be obtained by subjecting the subject to preliminary spirometric testing prior to putting the subject on the ventilator and determining a spirometric standard for the subject from the results of the preliminary spirometric testing. This may be done, for example, if the subject is to be put on a respiratory ventilator during a surgical procedure. In this case, the subject is subjected to preliminary spirometric testing prior to the operation when the subject is fully conscious and breathing normally. During the surgical procedure when the subject is anesthetized and ventilated by a ventilating machine, the ventilating machine is operated so that the ventilation of the subject conforms to the subject's breathing as determined in the preliminary spirometric testing. The spirometric assessment is preferably performed by the same method as the preliminary spirometric testing. For example, the spirometric standard may be obtained by preliminary spirometric testing performed by placing one or more microphones on the subject's body over the respiratory tract and analyzing acoustic signals generated by the microphones as disclosed in Applicant's co-pending application Ser. No. 10/771,139, entitled, "Method and system for analyzing respiratory tract air flow", filed on Feb. 4, 2004, which is incorporated herein in its entirety by reference. The subject is then placed on the ventilator (without removing the microphones) and the spirometric assessment performed by the same method.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Thus, in its first aspect, the present invention provides a computer implemented method for operating a respiratory ventilator ventilating a subject comprising:
(a) obtaining one or more body signals from the subject indicative of the subject's ventilation;
(b) analyzing the one or more signals so as to perform a spirometric assessment of the ventilation; and
(c) determining whether the spirometric assessment conforms to one or more predetermined spirometric standards.

In its second aspect, the invention provides a computer implemented method for operating a respiratory ventilator ventilating a subject comprising:
(a) analyzing one or more body signals from the subject indicative of the subject's ventilation so as to perform a spirometric assessment of the ventilation; and
(b) determining whether the spirometric assessment conforms to one or more predetermined spirometric standards In its third aspect the invention provides a system for ventilating a subject comprising;
(a) a respiratory ventilator;
(b) one or more sensors configured to be fixed onto the subject's body generating one or more signals indicative of the ventilation of the subject; and
(c) a processor configured to:
   i) analyze the one or more signals so as to perform a spirometric assessment of the ventilation; and
   ii) determine whether the spirometric assessment conforms to one or more predetermined spirometric standards.

In its fourth aspect, the invention provides a program storage device readable by machine, tangibly embodying a program of instructions executable by the machine to perform method steps for operating a respiratory ventilator ventilating a subject comprising:
(a) analyzing one or more body signals from the subject indicative of the subject's ventilation so as to perform a spirometric assessment of the ventilation; and
(b) determining whether the spirometric assessment conforms to one or more predetermined spirometric standards.

In its fifth aspect, the invention provides a computer implemented computer program product comprising a computer useable medium having computer readable program code embodied therein for operating a respiratory ventilator ventilating a subject the computer program product comprising:
computer readable program code for causing the computer to analyze the one or more signals so as to perform a spirometric assessment of the ventilation; and
computer readable program code for causing the computer to determine whether the spirometric assessment conforms to one or more predetermined spirometric standards.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
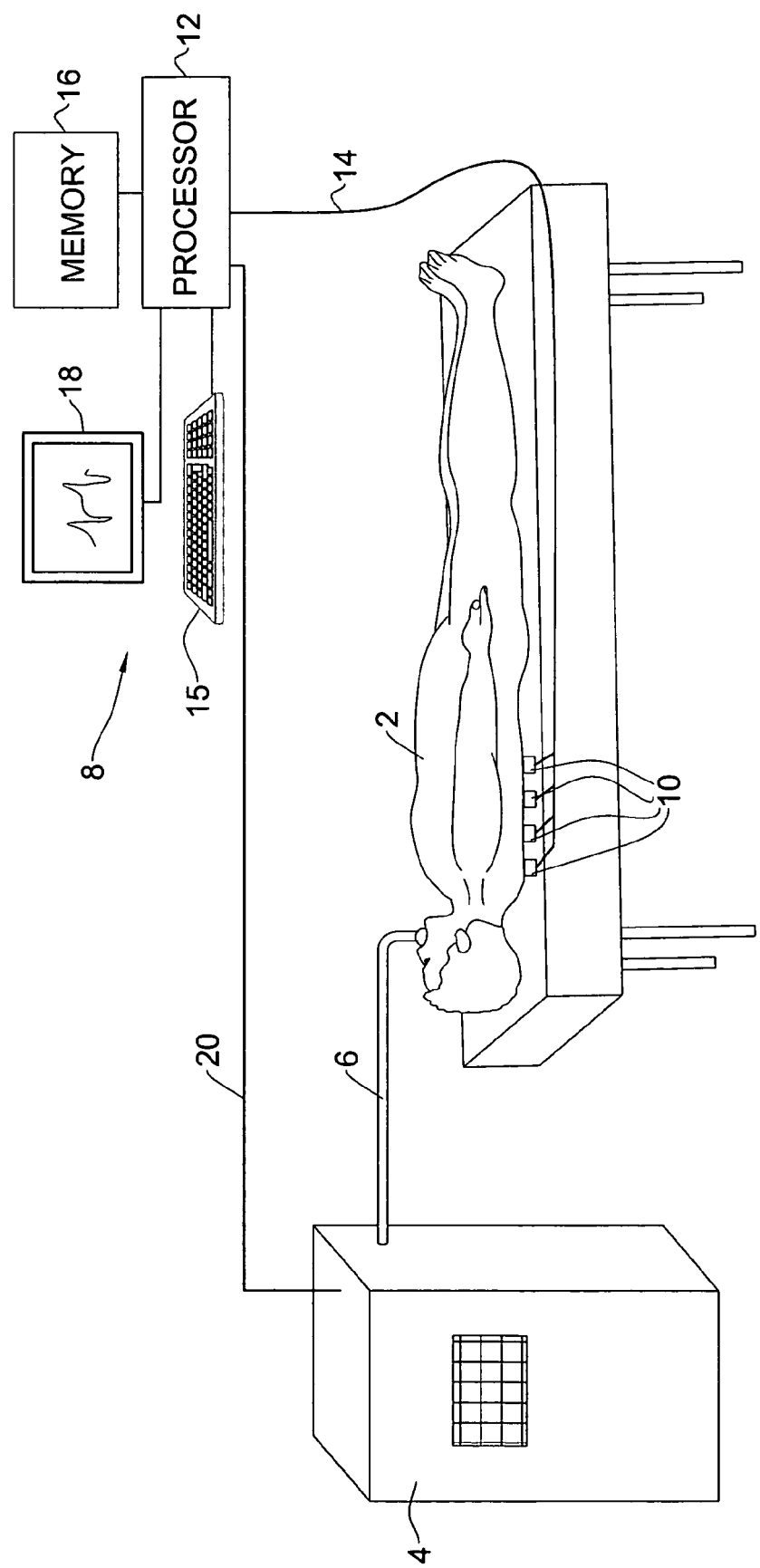
FIG. 1 shows a system for ventilating a subject, in accordance with one embodiment of the invention.

FIG. 1 shows a system 1 for ventilating a subject 2, in accordance with one embodiment of the invention. The system 2 comprises a respiratory ventilator 4 that cycles air into and out of the subject's respiratory system via a tube 6. The system 1 also includes a subsystem 8 for obtaining and analyzing signals indicative of the subject's breathing. The subsystem 8 induces one or more sensors 10 configured to be affixed to the subject's body over the subject's respiratory tract, for example, on the subject's back. The sensors 10 generate voltage signals indicative of the patient's ventilation, and may be, for example, microphones that detected respiratory tract sounds. The transducers 10 may be applied to the subject by any means known in the art, for example using an adhesive, suction, or fastening straps. The subsystem 8 also includes a processor 12. Signals generated by the sensors 10 are input to the processor 12 via an electric cable 14. An input device such as a computer keyboard 15 is used to input relevant information relating to the examination such as personal details of the individual 2.

The processor 12 is configured to analyze the input signals in order to obtain a spirometric assessment of the subject's ventilation. The spirometric assessment is compared to a spirometric standard previously stored in a memory 16 associated with the processor 12. The subsystem 8 may also include a display monitor 18 for displaying the spirometric assessment, the spirometric standard or a comparison of the spirometric assessment and standard. The display 18 may also be used to display images of the subject's respiratory tract.

The processor 12 is also configured to control the operation of the ventilator 4 via an electrical cable 20. If the processor 12 determines from the comparison of the spirometric assessment and standard that the ventilation of the subject does not conform to the standard, the processor 12 adjusts the operating parameters of the ventilator 4 so that the ventilation of the subject conforms to the spirometric standard. The processor 12 may adjust, for example, the flow rate of air into or out of the subject's respiratory tract, the duration of the inspiratory phase and or the duration of the expiratory phase.

In a preferred embodiment a spirometric assessment is obtained at a plurality of times during each respiratory cycle, and each assessment is compared to a spirometric standard stored in the memory 16. Following each comparison, the operating parameters 4 are adjusted, as explained above. In this way, the subject's ventilation is continuously monitored and maintained in conformity with the one or more spirometric standards stored in the memory 16.

Figure 2:
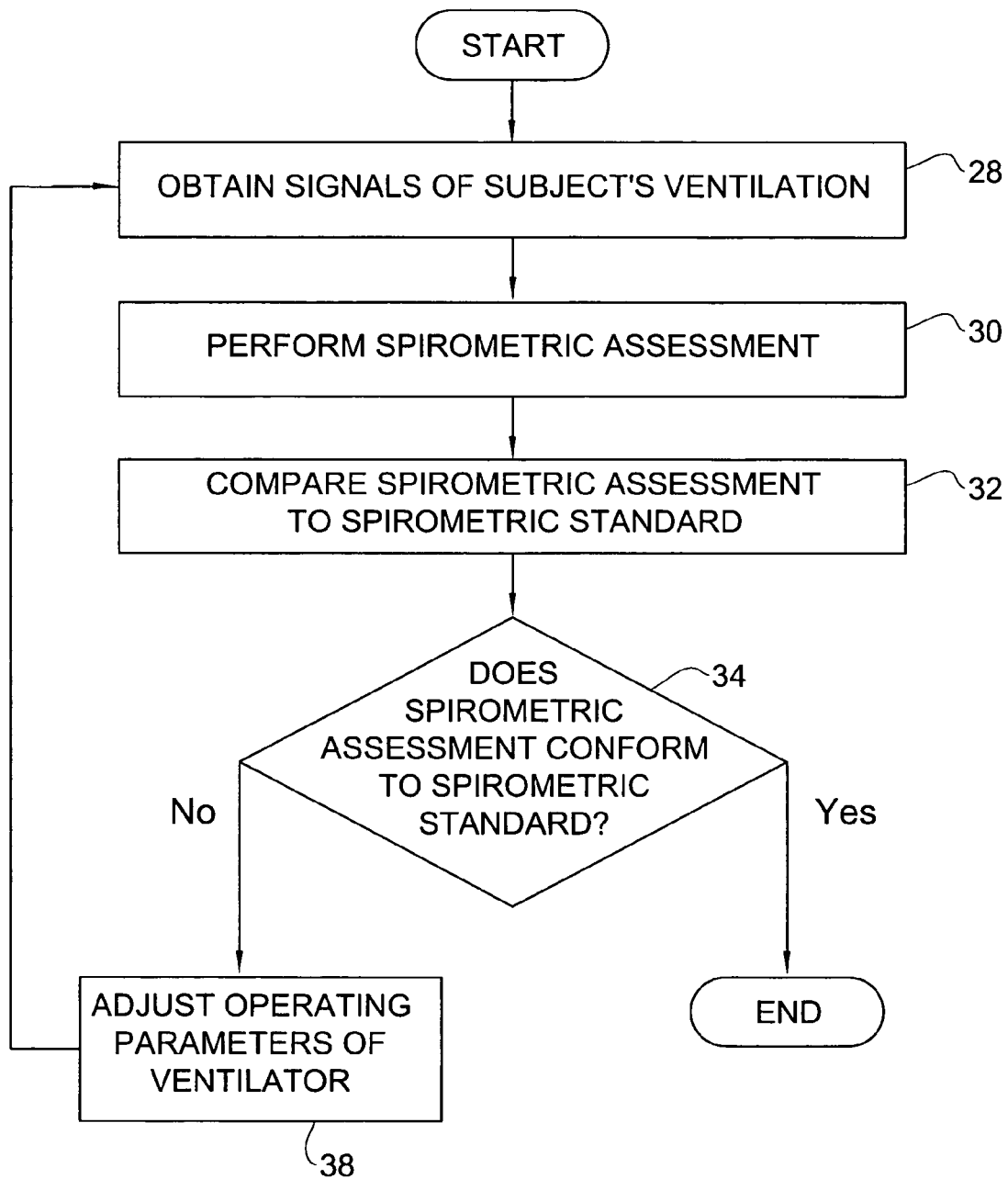
FIG. 2 shows a flow chart for ventilating a subject in accordance with one embodiment of the method of the invention.

FIG. 2 shows a flowchart showing a method for carrying out the method of the invention. In step 28, one or more signals are obtained indicative of the ventilation of the subject. In step 30 a spirometric assessment of the input signals is performed. In step 32, the results of the spirometric assessment are compared to a spirometric standard. In step 34 it is determined whether the spirometric assessment conforms to the spirometric standard. If yes, the process terminates (step 36). If no, the operating parameters of the ventilator are adjusted (step 38) and the process returns to step 28. As stated above, each of the subject's respiratory cycles may be divided into a plurality of time intervals and the process of FIG. 2 applied to each time interval.

In a preferred embodiment of the invention, the sensors 10 are sound transducers. In this case, each transducer 10 produces an analog voltage signal indicative of pressure waves arriving to the transducer. The acoustic signals are transmitted to the processor 12 over the cable 14 over a time interval from $t_0$ to $t_m$. The analog signals are digitized by a multichannel analog to digital converter. The digital data signals $P(x_i, t)$ thus represent the pressure wave at the location xi of the ith transducer (i=1 to N, where N is the number of transducers 10) at time t. The signals may be denoised by the processor 12 by filtering components having frequencies outside of the range of respiratory sounds, for example, vibrations due to movement of the individual, or cardiac sounds. Each signal may also be subject to band pass filtering by the processor 12 so that only components in the signal within a range of interest are analyzed. The input device 14 may be used to input a subdivision of the time interval $t_0$ to $t_m$ into subintervals $t_0, t_1, t_2, \ldots t_m$. Alternatively, the times $t_2, \ldots t_{m-1}$ may be determined automatically by the processor 12.

In this preferred embodiment, the system 1 is used to obtain the spirometric standard in a preliminary spirometric test as well as to perform the spirometric assessment. Obtaining the spirometric standard as well as performing the spirometric assessment involves determining an average acoustic energy $\tilde{P}(x, ti, ti+1)$ over each subinterval from $t_i$ to $t_{i+1}$, i=0 to m-1 at the plurality of locations x in a calculation involving at least one of the signals $P(x_i, t)$. The average acoustic energy $\tilde{P}(x, ti, ti+1)$ is preferably determined as disclosed in Applicant's co-pending application Ser. No. 10/338,742, entitled, "Method and system for analyzing respiratory tract air flow", filed on Feb. 4, 2004. The functions $\tilde{P}(x, ti, ti+1)$ are then integrated with respect to x, $$\sum_x \tilde{P}(x, t_i, t_i+1)$$

in order to obtain a total flow rate of air in the airways during the interval from $t_i$ to $t_{i+1}$. The functions $$\sum_x \tilde{P}(x, t_i, t_i+1)$$

are then integrated with respect to time, $$\sum_{t0}^{tk} \sum_x \tilde{P}(x, t_i, t_i+1),$$

in order to obtain the total volume of air that has flowed in the airways from $t_0$ to $t_k$, for each k from 1 to m.

The processor 12 may also configured to display on the display device 18 a spirometry curve which is a plot of the flow rate $$\sum_x \tilde{P}(x, t_i, t_i+1)$$

during the interval from $t_i$ to $t_{i+1}$ as a function of the volume $$\sum_{t0}^{tk} \sum_x \tilde{P}(x, t_i, t_i+1)$$

during the same time interval.

The invention claimed is:

1. A computer implemented method for operating a respiratory ventilator ventilating a subject comprising:
   (a) obtaining one or more body signals from the subject indicative of the subject's ventilation;
   (b) analyzing the one or more signals so as to perform a spirometric assessment of the ventilation; and
   (c) determining whether the spirometric assessment satisfactorily conforms to one or more predetermined spirometric standards
   wherein the spirometric standard is obtained by determining a total acoustic energy on a body surface overlying the subject's respiratory tract.

2. A computer implemented method for operating a respiratory ventilator ventilating a subject comprising:
   (a) analyzing one or more body signals from the subject indicative of the subject's ventilation so as to perform a spirometric assessment of the ventilation; and
   determining whether the spirometric assessment satisfactorily conforms to one or more predetermined spirometric standards wherein the spirometric standard is obtained by determining a total acoustic energy on a body surface overlying the subject's respiratory tract.

3. The method according to claim 1 further comprising adjusting one or more operating parameters of the ventilator if the spirometric assessment does not satisfactorily conform to the spirometric standard, so as to make the spirometric assessment better conform to the spirometric standard.

4. The method according to claim 3 further comprising repeating steps (a), (b), and (c) as required so as to make the spirometric assessment satisfactorily conform with the spirometric standard.

5. The method according to claim 1 wherein the signals are acoustic signals.

6. The method according to claim 5 wherein the spirometric assessment comprises determining a total acoustic energy on a body surface overlying the subject's respiratory tract.

7. The method according to claim 1 wherein the spirometric standard is obtained in a preliminary spirometric testing of the subject prior to the ventilation.

8. The method according to claim 3 wherein the operating parameters of the ventilator are selected from: (a) an air flow rate into the subject's respiratory tract; (b) an air flow rate out of the respiratory tract; (c) a duration of an inspiratory phase of a respiratory cycle; (d) respiratory rate; (e) inspiration/expiration ratio; (f) positive end-expiratory pressure; and (g) a duration of an expiratory phase of a respiratory cycle.

9. A system for ventilating a subject comprising;
 (a) a respiratory ventilator;
 (b) one or more sensors configured to be fixed onto the subject's body generating one or more signals indicative of the ventilation of the subject; and
 (c) a processor configured to: i) analyze the one or more signals so as to perform a spirometric assessment of the ventilation; and ii) determine whether the spirometric assessment satisfactorily conforms to one or more predetermined spirometric standards
 wherein the spirometric standard is a total acoustic energy on the body surface.

10. The system according to claim 9 wherein the processor is further configured to iii) adjust one or more operating parameters of the ventilator if the spirometric assessment does not conform to the spirometric standard so as to make the spirometric assessment better conform to the spirometric standard.

11. The system according to claim 10 wherein the processor is further configured to repeat steps i), ii) and iii) as required so as to make the spirometric assessment satisfactory conform with the spirometric standard.

12. The system according to claim 9 wherein the sensors are microphones generating acoustic signals.

13. The system according to claim 12 wherein performing the spirometric assessment comprises determining a total acoustic energy on a body surface overlying the subject's respiratory tract.

14. The system according to claim 9 wherein the spirometric standard is obtained by integrating an acoustic energy on the body surface.

15. The system according to claim 9 wherein the spirometric standard is obtained in a preliminary spirometric testing of the subject prior to the ventilation.

16. The system according to claim 10 wherein the operating parameters of the ventilator are selected from: (a) an air flow rate into the subject's respiratory tract; (b) an air flow rate out of the respiratory tract; (c) a duration of an inspiratory phase of a respiratory cycle; (d) respiratory rate; (e) inspiration/expiration ratio; (f) positive end-expiratory pressure; and (g) a duration of an expiratory phase of a respiratory cycle.

17. A program storage device readable by machine, tangibly embodying a program of instructions executable by the machine to perform method steps for operating a respiratory ventilator ventilating a subject comprising:
 i) analyzing one or more body signals from the subject indicative of the subject's ventilation so as to perform a spirometric assessment of the ventilation; and
 ii) determining whether the spirometric assessment conforms to one or more predetermined spirometric standards
 wherein the spirometric standard is obtained by determining a total acoustic energy on a body surface overlying the subject's respiratory tract.

18. A computer implemented computer program product comprising a computer useable medium having computer readable program code embodied therein for operating a respiratory ventilator ventilating a subject the computer program product comprising:
 computer readable program code for causing the computer to analyze the one or more signals so as to perform a spirometric assessment of the ventilation; and
 computer readable program code for causing the computer to determine whether the spirometric assessment conforms to one or more predetermined spirometric standards
 wherein the spirometric standard is obtained by determining a total acoustic energy on a body surface overlying the subject's respiratory tract.

* * * * *